United States Patent [19]
Gerzevske et al.

[11] Patent Number: 6,022,970
[45] Date of Patent: Feb. 8, 2000

[54] PROCESS FOR PREPARING 2-ANILINOACRIDONES

[75] Inventors: Kevin R. Gerzevske; Edward E. Jaffe, both of Wilmington, Del.

[73] Assignee: Ciba Specialty Chemicals Corporation, Tarrytown, N.Y.

[21] Appl. No.: 09/075,002

[22] Filed: May 8, 1998

Related U.S. Application Data

[60] Provisional application No. 60/059,418, May 9, 1997.

[51] Int. Cl.$^7$ ............... C07D 219/06; C07D 219/08; C09B 48/00
[52] U.S. Cl. ............................................. 546/103
[58] Field of Search ............................... 546/103

[56] References Cited

U.S. PATENT DOCUMENTS

| | | | |
|---|---|---|---|
| 4,286,998 | 9/1981 | Höltje et al. | 106/288 |
| 4,544,746 | 10/1985 | Höltje | 546/103 |
| 4,881,980 | 11/1989 | Dietz et al. | 106/495 |
| 4,937,345 | 6/1990 | Dietz et al. | 546/103 |

*Primary Examiner*—Alan L. Rotman
*Attorney, Agent, or Firm*—Kevin T. Mansfield

[57] ABSTRACT

An improved process for the preparation of optionally substituted 2-anilinoacridones from optionally substituted 2,5-dianilinoterephthalic acids, comprises:

(a) cyclizing 2,5-dianilinoterephthalic acid to give an intermediate product mixture which contains a major portion of a 2-anilino-3-carboxyacridone and a minor portion of a quinacridone;

(b) combining said intermediate product mixture with a solvent which dissolves the 2-anilino-3-carboxyacridone at elevated temperatures but does not dissolve the quinacridone;

(c) decarboxylating the 2-anilino-3-carboxyacridone in the mixture from step (b) at elevated temperatures to yield a product slurry comprising a solid quinacridone and a 2-anilinoacridone dissolved in the solvent;

(d) separating the solid quinacridone, the catalyst, and other solid impurities from the solvent, whereby a solution containing the dissolved 2-anilinoacridone is obtained; and (e) subsequently separating the dissolved 2-anilinoacridone from the solvent. This process provides 2-anilinoacridone in high yield and purity. A process for the preparation of 2-anilinoacridone/quinacridonequinone high performance golden yellow pigments is also described.

20 Claims, No Drawings

PROCESS FOR PREPARING 2-ANILINOACRIDONES

This application claims the benefit under 35 U.S.C. 119(e) of U.S. Provisional Application No. 60/059,418, Filed May 9, 1997.

This invention relates to a process for the preparation of optionally substituted 2-aryl-amino-9(10H)acridones, more commonly referred to as 2-anilinoacridones. More particularly it relates to an improved process for the preparation of 2-anilinoacridones in high yield and high purity from 2,5-dianilinoterephthalic acid or derivatives thereof.

2-Anilinoacridone is a known photostabilizer of quinacridonequinone, a high performance golden yellow pigment. Alone, quinacridonequinone is deficient in lighffastness properties. U.S. Pat. No. 3,160,510 discloses solid solutions of quinacridonequinone with quinacridone. Such pigment solid solutions exhibit good lighffastness properties. However, the quinacridone chromophore is brilliant red in hue and, in combination with the golden yellow quinacridonequinone, produces pigment colors which are maroon or brownish gold. As U.S. Pat. No. 4,286,998 discloses, 2-anilinoacridone stabilizes the quinacridonequinone chromophore very effectively. Since 2-anilinoacridone is a greenish-yellow solid, the hue of the quinacridonequinone pigment is not substantially altered by the addition of the 2-anilinoacridone as stabilizer, the mixture affording a golden yellow pigment. Most recently, solid solutions containing 2-anilinoacridone, quinacridonequinone and pyrrolo[3,4-c]pyrrole (DPP) components have also been shown to demonstrate excellent lightfastness properties, as disclosed in U.S. Pat. No. 5,472,496.

2-Anilinoacridone was first prepared by L. Kalb [Berichte 43, 2212 (1910)] via a two step process. First, N-phenyl-p-phenylenediamine was condensed with 2-chlorobenzoic add using amyl alcohol as the solvent and copper powder and cuprous chloride as catalysts to form the intermediate, 4'-phenylamino-2-carboxydiphenylamine, with dark blue by-products. This intermediate was cyclized to form crude 2-phenylamino-9(10H)acridone or 2-anilinoacridone, but it was difficult to separate the product from the impurities.

U.S. Pat. No. 4,258,190 discloses a general method for the preparation of acridones from 1,2,3,4-tetrahydro-7-arylamino-9(10H)acridones and precursors. Cyclohexanone is first condensed with an oxalate ester to give the corresponding 2-cyclohexanoneglyoxylate ester. The glyoxylate ester is decarbonylated to form the ester of 2-cyclohexanonecarboxylic acid. This ester is then condensed with an N-aryl-p-phenylenediamine in the presence of a catalytic amount of a strong acid to form a 2-[4'-(arylamino)]phenylaminocyclohexenecarboxylate ester. This ester in turn is cyclized in an inert high boiling liquid to give a 1,2,3,4-tetrahydro-7-aryl-amino-9(10H)acridone. This compound is dehydrogenated in an inert high boiling liquid in the presence of a catalytic amount of a supported palladium or platinum catalyst to afford a 2-anilinoacridone. In addition to the large number of synthetic steps required, handling of the pyrophoric and expensive palladium or platinum catalyst detracts from the practical utility of this process.

The first preparation of a 2-N-arylamino-3-carboxy-9(10H)acridone from a 2-N-arylamino-3-alkoxycarbonyl-1,4-dihydro-9(10H)acridone is reported in British Patent No. 1,382,259. This process suffers from a low yield of the carboxy acridone.

An alternative synthesis of compounds of the 2-N-arylamino-3-carboxy-9(10H)acridone class is disclosed in U.S. Pat. No. 4,544,746. In the presence of a mixture of polyphosphoric acid and phosphoric acid, 2,5-diarylaminoterephthalic acids are monocyclized under controlled conditions to give compounds having the general structure of a 2-anilino-3-carboxyacridone. A quinacridone is produced as a by-product which must be separated from the 2-anilino-3-carboxyacridone. This separation requires very high dilution in the presence of aqueous base to dissolve the free acid, followed by a filtration and subsequent acidification to liberate the purified 2-anilino-3-carboxyacridone. This sequence is not practical from an economic standpoint. The purification of 2-anilino-3-carboxyacridone by the procedure of U.S. Pat. No. 4,937,345, which still requires a 35 fold dilution with dilute aqueous base (relative to the dry weight of the acid), represents somewhat of an improvement, but is still economically disadvantageous.

U.S. Pat. No. 4,544,746 also discloses a process for the preparation of 2-arylamino-9(10)acridones or 2-anilinoacridones. Compounds with the general structure of a 2-anilinoacridone are prepared by dissolving the relevant, purified, derivative of 2-anilino-3-carboxyacridone in tetramethylene sulfone and heating it in the presence of basic cupric carbonate catalyst to effect decarboxylation. The dissolved 2-anilinoacridone is separated from the inorganic impurities by filtration and precipitated in an excess of water. Recrystallization is suggested as a means of purification, indicating that the 2-anilinoacridone as isolated is of inadequate purity.

Several disadvantages exist in the above-mentioned process. First, the decarboxylation step requires a purified 2-anilino-3-carboxyacridone. Purification of the 2-anilino-3-carboxyacridone is laborious and inefficient due to the low solubility of its sodium salt in water. Decarboxylation and isolation of the 2-anilinoacridone requires a minimum of two solvents for isolation and another solvent for recrystallization to achieve required purity.

Although decarboxylation of pure 2-anilino-3-carboxyacridone in tetramethylene sulfone does take place, the procedure has its drawbacks. First of all, filtration to remove the undissolved catalyst is required. Secondly, the 2-anilinoacridone is precipitated by adding the tetramethylene sulfone solution of 2-anilinoacridone into water, with which tetramethylene sulfone is miscible. However, recovery of tetramethylene sulfone for reuse from an aqueous solution is difficult and not cost effective. Thirdly, a "large excess" of water (about 200 fold based on dry isolated 2-anilinoacridone) is required to wash the precipitated 2-anilinoacridone nearly free of tetramethylene sulfone. Proper treatment of these wash waters from an environmental point of view entails additional costs. In addition, due to the presence of residual sulfur-containing impurities in the product, the purity of the 2-anilinoacridone obtained is unacceptable. Further purification is necessary before the product can be used.

The above patent teaches the advantage of tetramethylene sulfone as the solvent of choice, and states that decarboxylation of pure 2-anilino-3-carboxyacridone by a conventional decarboxylation reaction with a copper catalyst in quinoline or Dowtherm® as the reaction medium is generally unsatisfactory. Now, surprisingly, a process for the preparation of 2-anilinoacridone in high yield and high purity has been discovered which overcomes the deficiencies of the above described process, which process utilizes catalyst and solvent combinations that the above patent teaches as unsatisfactory.

Thus an improved process for the preparation of a 2-anilinoacridone of the formula I

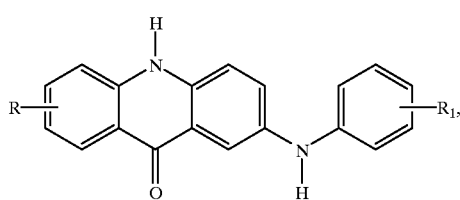

from a 2,5dianilinoterephtalic acid of the formula II

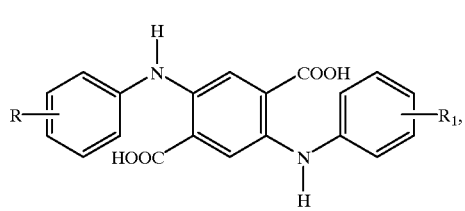

wherein R and $R_1$ in both formulas are each, independently, hydrogen, $C_1$–$C_4$alkyl, $C_1$–$C_4$alkoxy or halogen has been found which comprises the steps of:

(a) cyclizing the 2,5dianilinoterephtalic acid of the formula II to give an intermediate product mixture which contains a major portion of a 2-anilino-carboxyacridone and a minor portion of a quinacridone;

(b) combining said intermediate product mixture with an organic solvent which dissolves the 2-anilinoacridone of the formula I at elevated temperatures but does not dissolve the quinacridone;

(c) decarboxylating the 2-anilino-3carboxyacridone in the mixture from step (b) at elevated temperatures to yield a product slurry comprising a solid quinacridone and the 2-anilinoacridone of the formula I dissolved in the solvent;

(d) separating the solid quinacridone, insoluble catalyst, and other insoluble impurities from the solvent, whereby a solution containing the dissolved 2-anilinoacridone is obtained; and (e) subsequently separating the 2-anilinoacridone.

The overall reaction sequence for the simplest case, where R and $R_1$ are each hydrogen, is as follows:

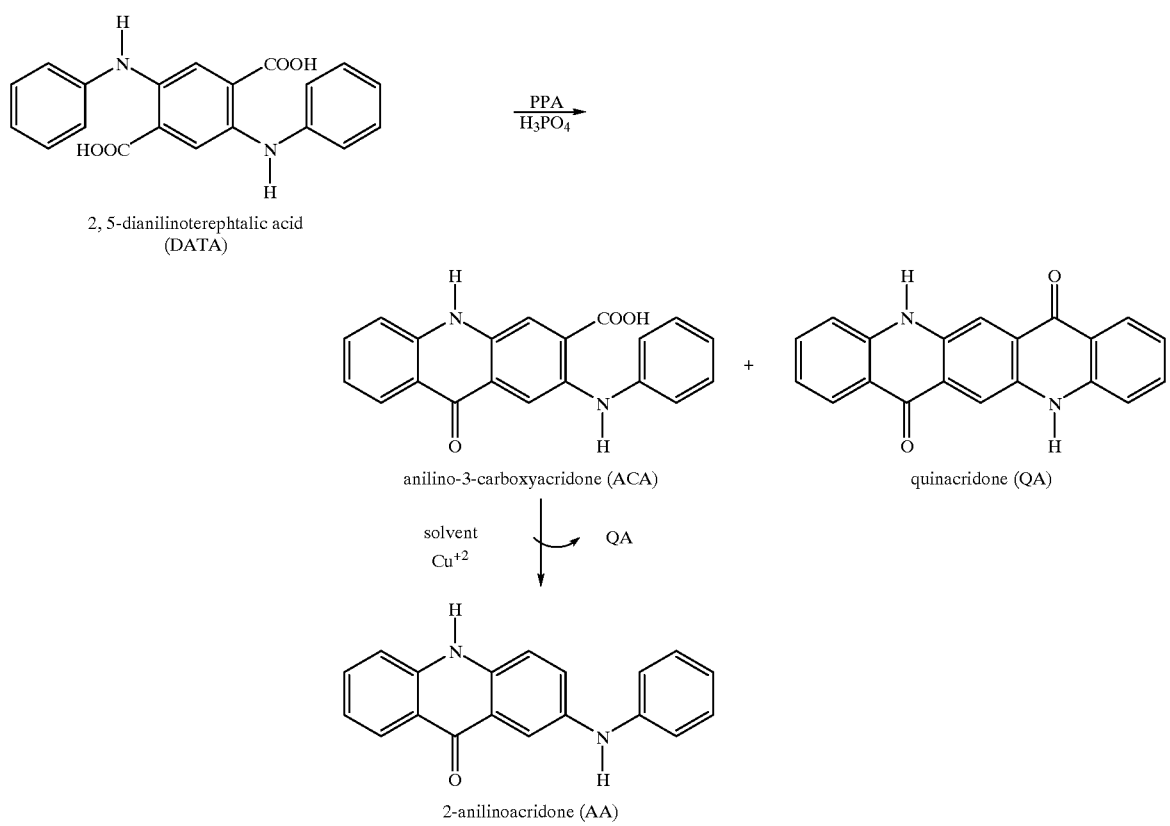

The starting material for the process, 2,5-dianilinoterephthalic acid, is monocyclized in polyphosphoric acid (PPA) of about 75–85% $P_2O_5$ strength at 80–90° C., under conditions known per se. However, the resultant solid mixture, which typically contains about 90% of 2-anilino-3carboxyacridone and 10% of quinacridone, is not separated before the subsequent decarboxylation reaction. Rather, this mixture is combined with a solvent which dissolves the 2-anilinoacridone final product at elevated temperatures but does not dissolve the quinacridone, and subjected directly to decarboxylation at elevated temperatures and in the presence of a decarboxylation catalyst. The resulting solution of 2-anilinoacridone in the solvent is then separated from the insoluble catalyst and the unaffected by-product quinacridone, preferably by filtration. The 2-anilinoacridone is which precipitates out is then isolated from the solvent.

The starting compounds required for the inventive process, optionally substituted 2,5-dianilinoterephthalic acids of the formula II,

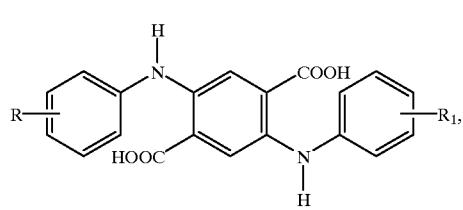

(II)

wherein R and $R_1$ are each, independently, hydrogen, $C_1$–$C_4$alkyl, $C_1$–$C_4$alkoxy or halogen, are known per se or can be made by known methods.

One skilled in the art will recognize that when R and $R_1$ are not hydrogen, more than one 2-anilinoacridone can be produced, for example, when R and $R_1$ are different or are substituents in the meta positon. Unless mixtures are desired, these circumstances should be avoided. Preferably R and $R_1$ are the same. Most preferably they are hydrogen.

R and $R_1$ as substituents are preferably the same and are $C_1$–$C_2$alkyl or $C_1$–$C_2$alkoxy or halogen. When the phenyl rings are substituted, they are preferably monosubstituted in the 2- or 4-position, or disubstituted in the 2,4 or 3,5-positions.

Preferred $C_1$–$C_2$alkyl and $C_1$–$C_2$alkoxy groups are methyl, ethyl and methoxy, especially 4-methyl. Preferably halogen is bromo, chloro or fluoro, especially 4-chloro.

In the first step, the monocyclization of the 2,5-dianilinoterephthalic acid to the 2-anilino-3-carboxyacridone is conveniently carried out in the presence of the defined amounts and specific concentrations of polyphosphoric acid taught in U.S. Pat. No. 4,937,345. These are a 5 to 15-fold, preferably 5 to 8-fold amount by weight, relative to the 2,5-dianilinoterephthalic acid, of polyphosphoric acid having concentration optimized to favor monocyclization, that is, having a $P_2O_5$ content in the range of 75 to 85%, preferably 78 to 82% and at a temperature in the range of 80–90° C.

The desired reaction, where R and $R_1$ are each hydrogen, is

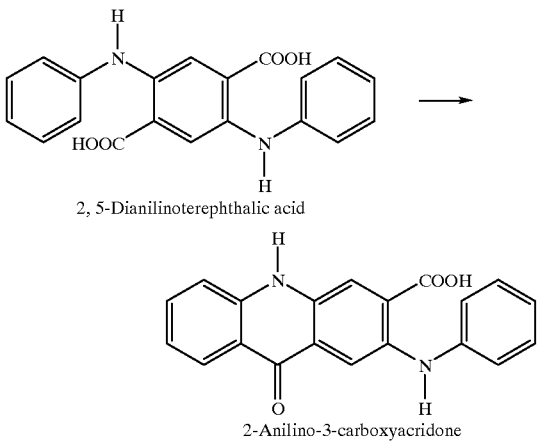

2, 5-Dianilinoterephthalic acid

2-Anilino-3-carboxyacridone

It is important to drive the reaction far enough to react all of the 2,5-dianilinoterephthalic acid. Generally this takes about 1 hour at about 85° C., at which point the reaction is stopped by cooling and combining the mixture with water. The resulting solid, suspended in the dilute aqueous phosphoric acid, is filtered and washed with water until neutral. However, even under optimized conditions for cyclization, a minor amount of quinacridone, the by-product formed by double cyclization of the 2,5-dianilinoterephthalic acid, is obtained, i.e.

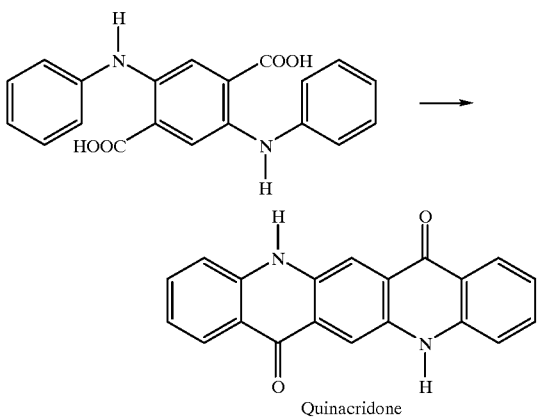

Quinacridone

Although quinacridone is a valuable red/violet commercial pigment, it must be removed in order to ultimately isolate the pure greenish-yellow 2-anilinoacridone. The prior art teaches to use the inherent physical solubility differences between 2-anilino-3-carboxyacridone and quinacridone to separate these two components prior to the decarboxylation of the 2-anilino-3-carboxyacridone to 2-anilinoacridone. Thus, U.S. Pat. No. 4,937,345 teaches that the cyclization reaction mixture containing 2-anilino-3-carboxyacridone and quinacridone is to be diluted with a 35-fold amount of water, relative to the dry weight of the organic compounds in the mixture. The 2-anilino-3-carboxyacridone is then dissolved over time by the addition of a base to the hot aqueous slurry. The quinacridone is removed by filtration; then the mother liquor is acidified with acetic acid to regenerate the solid 2-anilino-3-carboxyacridone product.

In practice this procedure is tedious and uneconomical. Obviously, the low concentration of the 2-anilino-3- carboxyacridone and quinacridone in the aqueous medium requires handling large volumes of material. Moreover, subtle variations also make the procedure difficult to practice. Once the 2-anilino-3-carboxyacridone has dissolved as the alkaline salt at elevated temperature, it will crystallize out of solution if allowed to cool because of its relatively low solubility in water. Redissolving the salt of 2-anilino-3-carboxyacridone again is observed to be very difficult in practice. To complicate the separation, the particle size of the by-product quinacridone is very small. This decreases the filtration rate and makes crystallization of the salt of 2-anilino-3-carboxyacridone from solution more likely, thus increasing the difficulty of the separation.

Surprisingly, it has now been found that removal of the by-product quinacridone prior to decarboxylating the 2-anilino-3-carboxyacridone is not necessary. On the contrary, decarboxylation of the 2-anilino-3-carboxyacridone is not inhibited by the presence of quinacridone. The 2-anilino-3-carboxyacridone/quinacridone mixture is slurried in an organic solvent which is a solvent for the 2-anilinoacridone of the formula I at elevated temperatures but does not dissolve the quinacridone. With an appropriate solvent, good decarboxylation results are obtained when the intermediate product mixture contains up to 20 percent by weight of quinacridone, that is, from 80 to 98 percent by weight of 2-anilino-3-carboxyacridone and from 20 to 2 percent by weight of quinacridone, based on the combined weight of 2-anilino-3carboxyacridone and quinacridone in the mixture. Preferably, the intermediate product mixture contains from 85 to 98 percent by weight of 2-anilino-3-carboxyacridone and from 15 to 2 percent by weight of quinacridone. Most preferably it contains at least 88 percent by weight of 2-anilino-3-carboxyacridone, based on the combined weight of 2-anilino-3-carboxyacridone and quinacridone in the mixture.

In addition to dissolving the 2-anilinoacridone but not the quinacridone at elevated temperatures, an appropriate solvent is one that has a boiling point above 200° C. Preferably the solvent has a boiling point in the range from 220 to 290° C. so that the decarboxylation can be carried out without resort to pressure. Preferably the solvent will also dissolve the 2-anilino-3-carboxyacridone at elevated temperatures. Additionally, the solvent should be inert under the rather extreme reaction conditions. Advantageously, it should also be inexpensive and relatively easy to recover and reuse. Finally, the solvent should dissolve significant quantifies of 2-anilinoacridone, for example up to 15% or more by weight when hot (≈220° C.), and very little when cooled to room temperature, preferably 0.2% or less for example.

One suitable class of solvents is aromatic hydrocarbons which are unsubstituted or substituted by $C_1$–$C_4$alkyl groups. This includes liquid aromatic hydrocarbons such as cyclohexylbenzene, α-methylnaphthalene, tetralin and mixtures thereof. It also includes solid aromatic hydrocarbons such as diphenylmethane, β-methylnaphthalene and biphenyl. However, these latter are preferably employed in admixture with each other or other suitable solvents which decrease their melting points.

Another suitable class of solvents is aromatic ethers which are unsubstituted or substituted by $C_1$–$C_4$alkyl groups, such as diphenyl ether and alkyl derivatives thereof.

A preferred class of solvents comprises one or more aromatic hydrocarbons in admixture with one or more aromatic ethers. An especially preferred solvent of this type is a mixture of diphenyl ether and biphenyl, in particular a eutectic mixture of diphenyl ether and biphenyl having a boiling point of about 258° C. This eutectic mixture is commercially available under various tradenames such as Dowtherm® A (from Dow Chemical Co.) and Therminol® VP-1 or simply Therminol (from the Monsanto Co.).

It is known from U.S. Pat. No. 4,258,190 that 2-anilinoacridone is soluble in hot Dowtherm. It is also known that quinacridone is very insoluble in most common solvents, including Dowtherm. However, U.S. Pat. No. 4,544,746 teaches, in col. 3, lines 48–53, "The decarboxylation of [purified] ACA [2-anilino-3-carboxyacridone] by conventional, heterogeneous decarboxylation reactions with copper catalyst and quinoline or Dowtherme as reaction medium is generally unsatisfactory. Partial product degradation occurs, and the separation of the product from the catalyst is difficult and the overall yield is relatively low." Surprisingly, however, it has been found that the decarboxylation of 2-anilino-3-carboxyacridone in the presence of quinacridone, with subsequent purification of the 2-anilinoacridone solution by a hot filtration to remove the undesired quinacridone, proceeds very well in such a solvent. Additionally, this solvent is suitable, as a part of the process, for the crystallization of 2-anilinoacridone.

The amount of solvent employed is not critical. The amount to employ should be sufficient to provide adequate stirrability during the reaction and complete solubility of the 2-anilinoacridone at temperatures suitable for the hot filtration. In practice about 8 to 30-fold amounts by weight, preferably 10 to 16-fold amounts by weight, relative to the 2-anilino-3-carboxyacridone/quinacridone mixture, provide good results.

The decarboxylation reaction is carried out by heating the mixture of the intermediate product reaction mixture and solvent to a temperature above about 200° C., advantageously from 220 to 290° C. and especially from 230 to 270° C., in the presence of a decarboxylation catalyst. The reaction can be carried out with or without a blanket of nitrogen. Preferably a nitrogen blanket is employed.

Suitable decarboxylation catalysts are copper (II) salts such as copper carbonate and copper hydroxide. Use of commercial-grade basic copper (II) carbonate, $CuCO_3Cu(OH)_2$, as the decarboxylation catalyst works very well and is preferred. Suitable amounts of a decarboxylabon catalyst are 1 to 6% by weight, relative to the 2-anilino-3-carboxyacridone/quinacridone mixture. Advantageously, from 1 to 3% by weight, especially about 1.5% of basic copper (II) carbonate by weight, relative to the 2-anilino-3-carboxyacridone/quinacridone mixture, is employed.

Since the mixture of 2-anilino-3-carboxyacridone and quinacridone is filtered from a strongly acidic environment, care must be taken to remove all of the free phosphoric acid. If the 2-anilino-3-carboxyacridonelquinacridone presscake is not washed free of phosphoric acid, the decarboxylation will be adversely affected due to incapacitation of the catalyst.

The decarboxylation reaction is conveniently monitored by thin layer chromatography (TLC). Under the preferred reaction conditions, complete conversion of the 2-anilino-3-carboxyacridone to 2-anilinoacridone is observed after 1 to 2 hours. Then the suspended solids, that is, the quinacridone, any copper catalyst, and any other insoluble impurities, are removed from the reaction mixture while it is still hot. Conveniently, this is carried out by a hot filtration but other means, such as a centrifugation/decantabon may also be employed. Decolorizing carbon can optionally be added to the mixture after decarboxylation and prior to hot filtrabon; however, yield is sacrificed for a minimal purity improvement.

The 2-anilinoacridone is then precipitated from the clarified solution by addition of a non-solvent or, preferably, by cooling the solution to about room temperature and then isolating the 2-anilinoacridone crystals by filtration. The wetcake is then washed with a low boiling organic liquid such as acetone, methanol, or petroleum distillates to afford 2-anilinoacridone. The purity of the 2-anilinoacridone after washing is greater than 95% and is satisfactory for use in pigment preparations such as those described in U.S. Pat. No. 5,472,946. The final product is virtually free of quinacridone impurities. Typical values of quinacridone are less than or equal to 0.2%, generally less than 0.1%, by weight in the isolated 2-anilinoacridone product after crystallizabon, filtration and washing.

To evaluate its suitability for stabilizing quinacridonequinone, 2-anilinoacridone prepared by the method of this invention was incorporated into a transparent golden quinacridonequinone solid solution via conventional techniques. Thus the two components, 2-anilinoacridone and quinacridonequinone, were dissolved in concentrated sulfuric acid and then precipitated into water or another suitable nonsolvent. The solid solution obtained by this route is generally highly aggregated and very small in particle size. Therefore, solid solutions prepared by acid precipitation are often recrystallized, for example, by heating the aqueous acid suspension of the pigment in the presence or absence of an organic solvent. The pigments prepared by acid precipitation are optionally further subjected to a crystal growth step, which is promoted by a variety of surfactants and/or organic solvents according to procedures known in the pigment art.

A sample of 2-anilinoacridone, prepared as disclosed in U.S. Pat. No. 4,258,190, was also combined with quinacridonequinone in an analogous manner as a control. Both samples were dispersed into a solventbome basecoat-clearcoat paint system at 16% pigment concentration and evaluated for both coloristic and outdoor durability properties. The coloristic and long term durability differences in both metallic and tint ($TiO_2$) extensions between the sample according to the present invention and the control were experimentally insignificant.

The 2-anilinoacridone prepared via this invention also shows satisfactory results in evaluations in pigments similar to those disclosed in U.S. Pat. No. 5,472,496.

The following examples illustrate the invention. However the invention is not limited thereto.

EXAMPLE 1. (Comparison)

A. Preparation of Purified 2-anilino-3-carboxyacridone 1272 gm of 115% polyphosphoric acid (83.8% $P_2O_5$) and 46 ml of water ($P_2O_5$=80.8%, after dilution) are charged into a dry reactor equipped with an agitator, thermometer and drying tube. The temperature is adjusted to 75° C. and allowed to stabilize before beginning incremental additions (5 min. increments of about 9.2 gm per addition) of 220 gm of 2,5-dianilinoterephthalic acid over a period of 2 hours. The temperature is kept between 75 and 85° C. during the addition. After completion of the addition, the solution is kept at 85° C. for 1 hour; then added to 2.2 L of water at 20° C., using an additional 1.8 L of water to aid in removing all of the remaining solution from the reaction flask. Then with simple stirring, the resulting slurry is heated to 80–90° C. and kept at that temperature for 1–2 hours, during which time all of the phosphate salt of 2-anilino-3-carboxyacridone hydrolyzes and the crude product mixture becomes bright orange. The solid is filtered and washed until the pH of the filtrate is neutral.

To remove the undesired quinacridone from the 2-anilino-3-carboxyacridone, the presscake is reslurried in 4 L of water and heated to 85–90° C. Then sufficient 50% NaOH is added to adjust the pH to greater than 11. The mixture is stirred and heated for 1 hr. to allow the 2-anilino-3-carboxyacridone to dissolve completely. The insoluble quinacridone is removed by filtration and washed with hot water to dissolve any remaining salt of 2-anilino-3-carboxyacridone. During the filtration, there is a tendency for the sodium salt of the 2-anilino-3-carboxyacridone to crystallize out on the funnel, which slows the filtration considerably. The yield of recovered quinacridone is 11–22 gm or 5 to 10%. The clear orange filtrates are combined and heated to 50–60° C. before acidifying with glacial acetic acid to bring the pH to about 4. This causes the orange product to precipitate. Heating at 50–60° C. is continued for 15 min. while monitoring the pH to ensure complete acidification. The pH is adjusted to 4 with dilute acetic acid. If acidification is not complete and some sodium salt of the 2-anilino-3-carboxyacridone remains, incomplete decarboxylation is observed in the subsequent reaction. The 2-anilino-3-carboxyacridone is isolated by filtration, washed acid free and dried to give 181–184 gm of product or an 87–88% yield.

B. Preparation of 2-anilinoacridone According to the Invention, but using Purified 2-anilino-3-carboxyacridone 50 gm of 2-anilino-3-carboxyacridone from step A, 1.25 gm basic cupric carbonate, $CuCO_3Cu(OH)_2$, and 660 gm Therminol® VP-1 (from the Monsanto Co.) are charged into a reaction flask equipped with an agitator, thermometer, Dean-Stark tube, reflux condenser, and a nitrogen source. The slurry is purged with nitrogen for 20 min. to deoxygenate the system. The vessel is evacuated three times under vacuum and then placed under a slow stream of nitrogen. The orange slurry is then slowly heated to reflux (≈258° C.). The solid, purified 2-anilino-3-carboxyacridone dissolves completely above 200° C., forming an orange solution. The first 20 ml of Therminol/water are collected in the Dean Stark tube and discarded to remove residual water. Reflux is continued for one hour. The solution turns a dark yellow color as the reaction progresses. The progress of the reaction is monitored by TLC. The reaction is complete when all of the 2-anilino-3-carboxyacridone has disappeared. The temperature is allowed to drop to 240° C.; then 10 gm decolorizing charcoal is added, followed by stirring for another 10 min. To aid in laboratory filtration, 10 gm of Celite® is added before filtering the solution hot on a fritted glass funnel. While the stirred filtrate is cooled to room temperature (≈25° C.), the product crystallizes out of solution. After cooling to room temperature, the crystallized product is isolated by filtration. The crude product is reslurried in 142 gm methanol and heated to 40° C. before cooling, filtering and washing with 50 gm methanol. This crude product is reslurried again in 50 gm methanol, filtered, and washed with 25 gm methanol. After drying, 31 gm of the product is obtained, corresponding to a 73% yield based on 2-anilino-3-carboxyacridone and having a 99% purity relative to an internal standard.

EXAMPLE 2.

A. Preparation of 2-anilino-3-carboxyacridone without Quinacridone Removal 1272 gm of 115% polyphosphoric acid (83.8% $P_2O_5$) and 46 ml of water ($P_2O_5$=80.8%, after dilution) are charged into a dry reactor equipped with an agitator, thermometer and drying tube. The temperature is adjusted to 75° C. and allowed to stabilize before beginning incremental additions (5 min. increments of about 9.2 gm per addition) of 220 gm of 2,5-dianilinoterephthalic acid over a period of 2 hours. Continuous addition over several hours is preferred on a larger scale. The temperature is kept between 75 and 85° C.

during the addition. After completion of the addition, the solution is kept at 85° C. for 1 hour and then added to 4 L of water at 20° C. With simple stirring, the slurry is heated to 80–90° C. and kept at that temperature for 1–2 hours until all of the phosphate salt of 2-anilino-carboxyacridone has hydrolyzed. The crude product mixture becomes bright orange. The solid is filtered and washed with tap water until the pH of the filtrate is neutral. The product is dried in the oven at a temperature of 85° C. This product weighs 205 gm and is a mixture of 2-anilino-3-carboxyacridone/quinacridone mixture which analyzes for 91% 2-anilino-3-carboxyacridone and 8% quinacridone.

B. Preparation of 2-Anilinoacridone 50 gm of 2-anilino-3-carboxyacridone/quinacridone mixture (approximately 90% 2-anilino-3-carboxyacridone and 10% quinacridone) and 660 gm Therminol VP-1 are charged into a reaction flask equipped with an agitator, thermometer, Dean-Stark tube, reflux condenser, and a nitrogen inlet. The solvent is purged by bubbling nitrogen into the slurry for 30 min. to deoxygenate the system. The vessel is evacuated three times under vacuum and then placed under a slow stream of nitrogen. The orange slurry is heated to 220° C. before the addition of 0.75 gm of basic cupric carbonate and then heated to reflux. A small amount (ca. 20 ml) of Therminol/water is distilled off into the Dean Stark tube and discarded to remove residual water from the system. Slow reflux is continued for 1–2 hr. The reaction progress is monitored by thin layer chromatography (TLC). When the reaction is complete, the temperature of the mixture is decreased to 240° C.; then it is filtered hot on a medium fritted glass funnel using 4 gm of Celite® as a filter aid. To remove any remaining 2-anilinoacridone, the funnel is flushed with an additional 150 ml of Therminol heated to 240° C. The quinacridone (ca. 7 gm of quinacridone, the catalyst, and other insoluble impurities, not including the filter aid), is removed in the hot filtration without any difficulty. As the filtered solution is cooled to room temperature, 2-anilinoacridone precipitates out of solution as a greenish-yellow solid. The product is separated from the Therminol by filtration. The Therminol-wet 2-anilinoacridone is reslurried in 140 gm methanol and filtered off from the Therminol/methanol mixture. This The crude wetcake is again similarly reslurried in 140 gm methanol before filtering off the remaining methanol and washing a final time with 25 gm methanol. Alternatively, the 2-anilinoacridone can be washed with methanol, acetone, or petroleum distillates on the funnel until the 2-anilinoacridone is free of Therminol. After drying and grinding, 32 gm of the product is obtained, an 81% yield based on the percentage of 2-anilino-3-carboxyacridone in the starting material. The purity of the 2-anilinoacridone is analyzed to be greater than 95%.

The methanol filtrates are combined and the methanol is separated via distillation. The remaining 2-anilinoacridone/Therminol slurry is added to the crystallization reactor prior to hot filtration. An additional 2 gm of 2-anilinoacridone is realized in the subsequent reaction, which amounts to an additional 5% increase in the yield of 2-anilinoacridone.

The Therminol and washes can be recycled in consecutive reactions, giving an overall isolated yield of 87% with no observed adverse effects on the quality of the resulting product.

Similar good results are obtainable when 2,5-dianilinoterephthalic acid is replaced by 2,5-di-p-toluidinoterephthalic acid or 2,5-di(4-chloroanilino)terephthalic acid.

EXAMPLE 3.

Incorporation of 2-anilinoacridone into a Golden-yellow Quinacridoneguinone Pigment.

Both a lab control using 2-anilinoacridone prepared according to U.S. Pat. No. 4,258,190 and a lab sample using 2-anilinoacridone prepared by the instant invention were converted to a golden-yellow pigment according to U.S. Pat. No. 4,286,998. The data on the color differences between the solventbome basecoaticlearcoats are demonstrated in Table I as well as outdoor durability data in Table II. The readings are expressed in CIELAB Color System units.

TABLE I

Color Differences Before Exposure of Pigment Made Using 2-Anilinoacridone According to the Present Invention Versus a Control 80/20 Metallic Basecoat/Clearcoat

| Sample ID | ΔE | ΔL | ΔA | ΔB |
|---|---|---|---|---|
| Lab Control | Control | Control | Control | Control |
| Lab Sample | 0.69 | 0.13 | −0.09 | 0.67 |

After one year of exposure in South Florida as shown in Table II, the durability results demonstrate that the 2-anilinoacridone prepared via this invention is a satisfactory substitute for the commercially proven anilinoacridone in this transparent golden yellow pigment.

TABLE II

12 Months South Florida Exposure Results: Color Differences vs. Corresponding Unexposed Samples. 80/20 Metallic Basecoat/Clearcoat

| Sample ID | ΔE | ΔL | ΔA | ΔB |
|---|---|---|---|---|
| Lab Control | 2.4 | −1.5 | 0.9 | −1.7 |
| Lab Sample | 2.2 | −1.4 | 0.9 | −1.5 |

What is claimed is:

1. A process for the preparation of a 2-anilinoacridone of the formula I

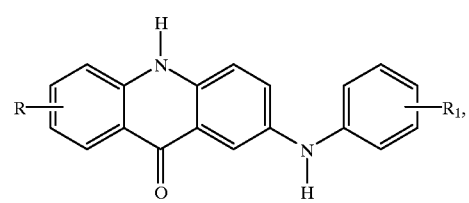

(I)

from 2,5-dianilinoterephthalic acid of the formula II

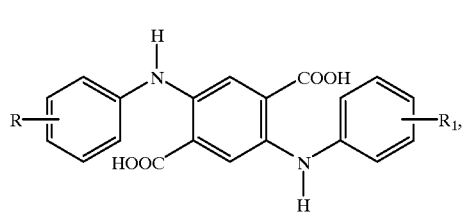

(II)

wherein R and $R_1$ in both formulas are each, independently, hydrogen, $C_1$–$C_4$alkyl, $C_1$–$C_4$alkoxy or halogen, which comprises the steps of:

(a) cyclizing the 2,5-dianilinoterephthalic acid of the formula II to give an intermediate product mixture which contains a major portion of a 2-anilino-3-carboxyacridone and a minor portion of a quinacridone;

(b) combining said intermediate product mixture with an organic solvent which dissolves the 2-anilinoacridone of the formula I at elevated temperatures but does not dissolve the quinacridone;

(c) decarboxylating the 2-anilino-3-carboxyacridone in the mixture from step (b) at elevated temperatures to yield a product slurry comprising a solid quinacridone and the 2-anilinoacridone of the formula I dissolved in the solvent;

(d) separating the solid quinacridone, the catalyst, and other insoluble impurities from the solvent, whereby a solution containing the dissolved 2-anilinoacridone is obtained; and (e) subsequently separating the 2-anilinoacridone from the solvent.

2. A process according to claim 1, wherein R and $R_1$ in both formulas are each hydrogen.

3. A process according to claim 1, wherein step (a) is carried out in polyphosphoric acid having a $P_2O_5$ content of 75 to 85%.

4. A process according to claim 1, wherein the intermediate product mixture contains from 80 to 98 percent by weight of 2-anilino-3-carboxyacridone and from 20 to 2 percent by weight of quinacridone, based on the combined weight of 2-anilino-3-carboxyacridone and quinacridone in the mixture.

5. A process according to claim 4, wherein the intermediate product mixture contains from 85 to 98 percent by weight of 2-anilino-3-carboxyacridone and from 15 to 2 percent by weight of quinacridone, based on the combined weight of 2-anilino-3-carboxyacridone and quinacridone in the mixture.

6. A process according to claim 1, wherein the solvent employed is suitable for crystallizing 2-anilinoacridone.

7. A process according to claim 1, wherein the solvent has a boiling point above 200° C.

8. A process according to claim 7, wherein the solvent has a boiling point in the range from 220 to 290° C.

9. A process according to claim 7, wherein the solvent is an aromatic hydrocarbon which is unsubstituted or substituted by $C_1$–$C_4$alkyl groups, an aromatic ether which is unsubstituted or substituted by $C_1$–$C_4$alkyl groups, or a mixture thereof.

10. A process according to claim 9, wherein the solvent is a mixture of diphenyl ether and biphenyl.

11. A process according to claim 10, wherein the solvent is a eutectic mixture of diphenyl ether and biphenyl.

12. A process according to claim 1, wherein step (c) is carried out by heating the intermediate product reaction mixture to a temperature above about 200° C. in the presence of a decarboxylation catalyst.

13. A process according to claim 12, wherein step (c) is carried out by heating the intermediate product reaction mixture to a temperature in the range from 220 to 290° C. in the presence of a decarboxylation catalyst.

14. A process according to claim 12, wherein the decarboxylation catalyst is a copper (II) salt.

15. A process according to claim 14, wherein the decarboxylation catalyst is basic copper (II) carbonate.

16. A process according to claim 1, wherein step (d) is carried out by hot filtration.

17. A process according to claim 1, wherein step (e) comprises precipitating the 2-anilinoacridone from solution and then isolating the 2-anilinoacridone by filtration and washing.

18. A process according to claim 17, wherein step (e) comprises precipitating the 2-anilinoacridone from solution by cooling the solution from step (d).

19. A process according to claim 18, wherein the 2-anilinoacridone isolated from step (e) contains less than 0.2 percent by weight of quinacridone.

20. A process for the preparation of a 2-anilinoacridone/quinacridonequinone solid solution, which comprises the steps of:

(a) cyclizing 2,5-dianilinoterephthalic acid to give an intermediate product mixture which contains a major portion of 2-anilino-3-carboxyacridone and a minor portion of quinacridone;

(b) combining said intermediate product mixture with an organic solvent which dissolves 2-anilinoacridone at elevated temperatures but does not dissolve quinacridone;

(c) decarboxylating the 2-anilino-3-carboxyacridone in the mixture from step (b) to yield a product slurry comprising solid quinacridone and 2-anilinoacridone dissolved in the solvent;

(d) separating the solid quinacridone, the catalyst and other insoluble impurities from the solvent, whereby a solution containing the dissolved 2-anilinoacddone is obtained;

(e) subsequently separating the dissolved 2-anilinoacridone from the solvent and filtering, washing and drying the separated 2-anilinoacridone;

(f) dissolving the 2-anilinoacridone from step (e) and quinacridonequinone in concentrated sulfuric acid, and then (g) combining the solution from step (f) with a liquid which is a nonsolvent for 2-anilinoacridone and quinacridonequinone, whereby a 2-anilinoacridone/quinacridonequinone solid solution is obtained.

* * * * *